United States Patent
Milbradt et al.

(10) Patent No.: US 6,881,399 B2
(45) Date of Patent: Apr. 19, 2005

(54) COSMETIC FORMULATIONS OF HAVING HIGH AQUEOUS SOLUBILITY AND LOW FLASH POINTS

(75) Inventors: Robert Milbradt, Wiesbaden (DE); Sonja Klein, Hattersheim (DE); Franz Xaver Scherl, Burgkirchen (DE); Erich Gatter, Kastl (DE); Adelgunde Oberhauser, Neuötting (DE)

(73) Assignee: Clariant GmbH, Frankfurt (DE)

( * ) Notice: Subject to any disclaimer, the term of this patent is extended or adjusted under 35 U.S.C. 154(b) by 218 days.

(21) Appl. No.: 10/171,032

(22) Filed: Jun. 12, 2002

(65) Prior Publication Data

US 2003/0026774 A1 Feb. 6, 2003

(30) Foreign Application Priority Data

Jun. 19, 2001 (DE) .......................... 101 29 225

(51) Int. Cl.[7] .............................. A61K 7/06; A61K 7/00; A61K 9/00; A61K 9/14
(52) U.S. Cl. ..................... 424/70.1; 424/47; 424/70.28; 424/400; 424/401; 424/489; 424/DIG. 1; 514/937
(58) Field of Search ................................ 424/489, 401, 424/400, 70.1, 70.28, 4 A, DIG. 1; 514/937

(56) References Cited

U.S. PATENT DOCUMENTS 5,051,251 A * 9/1991 Morita et al. ............ 424/70.28
5,674,832 A * 10/1997 Keys ........................... 510/504
5,714,136 A * 2/1998 Yahagi et al. ............. 424/70.19
5,888,488 A * 3/1999 Fukuchi .................... 424/70.12
6,106,578 A * 8/2000 Jones ............................ 8/406
6,562,356 B1 * 5/2003 Verite et al. ................ 424/401
6,572,846 B1 * 6/2003 Klein ....................... 424/70.28
6,607,715 B1 * 8/2003 Barinova et al. .......... 424/70.1
2001/0053376 A1 * 12/2001 Iwai et al. .................. 424/401

FOREIGN PATENT DOCUMENTS

| DE | 197 14 162 | 8/1998 |
|---|---|---|
| WO | WO 91/12880 | 9/1991 |
| WO | 00/28950 | 5/2000 |

OTHER PUBLICATIONS

Hawley's Condensed Chemical Dictionary, 13th ed, 1997, p. 844.*
English abstract for DE 19714162, Aug. 27, 1998.
English abstract for JP 61–249911, Nov. 7, 1986.
English abstract for JP 61–260011, Nov. 18, 1986.
English abstract for JP 2000–044441, Feb. 15, 2000.

* cited by examiner

*Primary Examiner*—Gary Kunz
*Assistant Examiner*—Marina Lamm
(74) *Attorney, Agent, or Firm*—Richard P. Silverman

(57) ABSTRACT

The invention provides compositions comprising
   a) at least one quaternary ammonium compound, and
   b) at least one polyhydric alcohol having 5 to 12 carbon atoms.

The compositions have low setting points, good solubility and dispersibility in aqueous media and a low flash point.

37 Claims, No Drawings

COSMETIC FORMULATIONS OF HAVING HIGH AQUEOUS SOLUBILITY AND LOW FLASH POINTS

The invention relates to compositions comprising quaternary ammonium compounds which have a low setting point, good solubility or dispersibility in aqueous media and a low flash point and are thus highly suitable for formulating quaternary ammonium compounds.

Cosmetic compositions, such as, for example, hair-treatment compositions, often comprise sparingly water-soluble quaternary ammonium compounds which have a long-chain alkyl or alkenyl group. Such compositions are usually formulated as aqueous dispersions, emulsions, microemulsions, gels or else in aerosol form and are used, for example, as shampoos, hair cures, hair rinses, etc.

For the manufacturer of such compositions, it is highly advantageous to prepare the quaternary ammonium compounds as compounded materials or formulations in the form of flakes, pellets or pastes which, as well as having a high cationic active ingredient content, have a low setting point and good solubility or dispersibility in aqueous media.

In accordance with the prior art, the above requirements can be achieved by adding short-chain alcohols, in particular isopropanol, in amounts of from 15 to 20% by weight. Because of their low boiling and flash points, however, such short-chain alcohols are problematical.

As described in WO 00/28950, the short-chain alcohols can be replaced by linear fatty alcohols (e.g. cetyl alcohol, lauryl alcohol, behenyl alcohol or stearyl alcohol). In order to lower the setting point or melting point of the mixtures to temperatures below 100° C., glycols, such as, for example, propylene glycol or 1,3-butanediol, are additionally added.

WO 00/28950 further emphasizes that the fatty alcohols are advantageously homogeneous fatty alcohols which contain less than about 10% by weight of another fatty alcohol.

WO 00/28950 further explains that replacement of the short-chain alcohols by glycols without the simultaneous addition of fatty alcohols leads to formulations which can not be pelleted.

SUMMARY OF THE INVENTION

Surprisingly, it has now been found that compositions comprising quaternary ammonium compounds and at least one polyhydric alcohol having 5 to 12 carbon atoms have low setting and melting points, good solubility and dispersability in aqueous media and a low flashpoint.

Surprisingly, the compositions can be free from fatty alcohols and linear or branched alcohols having 8 to 36 carbon atoms and are nevertheless sufficiently hard and brittle at room temperature to allow pelleting or flaking. The novel compositions are thus highly suitable for formulating quaternary ammonium compounds.

The invention provides compositions comprising
a) at least one quaternary ammonium compound according to formula (1)

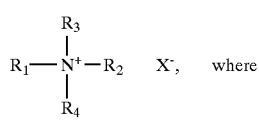

(1)

where $R_1$ is an unbranched or branched alkyl or alkenyl group having 12 to 36 carbon atoms, a group $R_5CONH(CH_2)_n$— or a group $R_5COO(CH_2)_n$—, where $R_5$ is an alkyl or alkenyl group having 12 to 36 carbon atoms and n is a number from 1 to 8, and $R_2$, $R_3$ and $R_4$, independently of one another, may be identical or different and are a —$CH_3$, $CH_3CH_2$—, $CH_3CH_2CH_2$—, $CH_3CH_2CH_2CH_2$—, —$CH_2CH_2OH$ or —$CH_2CH(OH)CH_2OH$ group and $X^-$ is an anion, and b) at least one polyhydric alcohol having 5 to 12 carbon atoms. In a preferred embodiment, the compositions are free from fatty alcohols and linear or branched monoalcohols having 8 to 36 carbon atoms.

DETAILED DESCRIPTION OF THE INVENTION

The proportion of quaternary ammonium compounds a), based on the finished compositions, is preferably 30 to 90% by weight, particularly preferably 40 to 85% by weight, especially preferably 45 to 85% by weight, very particularly preferably 60 to 82% by weight. Surprisingly, it has been found that the compositions can advantageously have high proportions by weight of quaternary ammonium compounds a) coupled with simultaneously low melting and setting points.

Quaternary ammonium compounds a) are preferably $(C_{12}-C_{36})$-alkyltrimethylammonium compounds, particularly preferably $(C_{14}-C_{30})$-alkyltrimethylammonium compounds, especially preferably $(C_{16}-C_{24})$-alkyltrimethylammonium compounds.

Particular preference is given to alkyltrimethylammonium compounds in which the alkyl radical is a behenyl, erucyl, cetyl or stearyl radical. The anion $X^-$ in formula (1) may be any desired charge-balancing anion; preferably chloride, iodide, bromide, methosulfate, hydrogensulfate, lactate and/or citrate, particularly preferably chloride and methosulfate.

A very particularly suitable quaternary ammonium compound a) is behenyltrimethylammonium chloride.

The proportion of polyhydric alcohols b) is, based on the finished compositions, preferably 10 to 70% by weight, particularly preferably 15 to 60% by weight, especially preferably 15 to 55% by weight.

Polyhydric alcohols b) are to be understood as meaning those which carry at least two OH groups in the molecule. The polyhydric alcohols b) may be unbranched or branched and saturated or unsaturated. In addition, the polyhydric alcohols b) can be constructed from low molecular weight polyhydric alcohols linked via ether bridges.

Suitable polyhydric alcohols b) are preferably pentanediol, hexanediol, hexylene glycol, trimethylpentanediol, heptanediol, octanediol, nonanediol, decanediol, undecanediol, dodecanediol, diglycerol, triglycerol, dipropylene glycol, tripropylene glycol, sorbitol, xylitol, mannitol and/or mixtures thereof.

Particularly preferred polyhydric alcohols b) are 1,5-pentanediol, 1,2-pentanediol, 1,6-hexanediol, 1,2-hexanediol, 1,7-heptanediol, 1,2-heptanediol, 1,8-octanediol, 1,2-octanediol, 1,9-nonanediol, 1,2-nonanediol, 1,10-decanediol, 1,2-decanediol, 1,11-undecanediol, 1,2-undecanediol, 1,12-dodecanediol, 1,2-dodecanediol, 2-methyl-2,4-pentanediol, 2,2,4-trimethyl-1,3-pentanediol, diglycerol, triglycerol, dipropylene glycol, tripropylene glycol, sorbitol, xylitol, mannitol and/or mixtures thereof.

Especially preferred polyhydric alcohols b) are 1,6-hexanediol, dipropylene glycol, 2-methyl-2,4-pentanediol, 2,2,4-trimethyl-1,3-pentanediol and mixtures thereof.

Particularly advantageous application properties are exhibited by compositions which comprise at least one polyhydric alcohol b) having 6 to 8 carbon atoms, which can optionally be used together with other polyhydric alcohols b).

Optionally, to improve the performance properties, the compositions according to the invention may comprise unbranched or branched monoalcohols having 1 to 4 carbon atoms.

Preferred monoalcohols are ethanol, propanol, isopropanol, butanol, isobutanol and tert-butanol, particularly preferably isopropanol.

Based on the finished compositions, the compositions preferably comprise less than 5% by weight, particularly preferably less than 3% by weight, of such monoalcohols.

In a preferred embodiment, the compositions are free from unbranched or branched monoalcohols having from 1 to 4 carbon atoms.

The compositions according to the invention preferably have setting points below 100° C., particularly preferably below 95° C., especially preferably below 90° C., very particularly preferably below 85° C.

The flash points of the compositions according to the invention are preferably above 80° C., particularly preferably above 100° C.

The compositions according to the invention may, for example, be pellets, flakes, extrudates, pastes, compacts, powders, and also emulsions or dispersions.

In a preferred embodiment, the compositions according to the invention are pellets or flakes, particularly preferably pellets.

In a preferred embodiment, the compositions according to the invention are prepared by preparing a mixture comprising i) at least one quaternary ammoniun compound a), optionally containing a branched or unbranched monoalcohol having 1 to 4 carbon atoms, ii) at least one polyhydric alcohol b) having 5 to 12 carbon atoms and iii) optionally at least one unbranched or branched monoalcohol having 1 to 4 carbon atoms.

In a preferred embodiment, the components i) to iii) are mixed and then heated, optionally with stirring. Here, the temperature is chosen so that the mixture is in the form of a melt. Preference is given to temperatures of from 70 to 120° C., particularly preferably 80 to 110° C. In another preferred embodiment, the component i) is introduced as a melt.

The quaternary ammonium compounds a) of component i) can be prepared in a known manner by alkylation of a tertiary amine in the presence of at least one unbranched or branched monoalcohol having 1 to 4 carbon atoms, preferably ethanol, propanol, isopropanol, butanol, isobutanol and tert-butanol, particularly preferably isopropanol. The quaternary ammonium compounds are preferably used as pellets or particularly preferably as powders. In a preferred embodiment, the quaternary ammonium compounds comprise less than 5% by weight, preferably less than 3% by weight, of monoalcohols. In a further preferred embodiment, the quaternary ammonium compounds comprise 10 to 25% by weight of monoalcohols. The compositions according to the invention preferably have a total content of unbranched or branched monoalcohols having 1 to 4 carbon atoms of less than 5% by weight, particularly preferably less than 3% by weight.

In a likewise preferred embodiment, the compositions according to the invention are free from unbranched or branched monoalcohols having 1 to 4 carbon atoms.

To establish the desired content of monoalcohols in the compositions according to the invention, the components i) and/or iii) are correspondingly chosen and calculated and/or the monoalcohols are partially or completely removed from the component i) beforehand.

In a further embodiment, the monoalcohols are subsequently removed from the compositions according to the invention except for the desired residual content. The monoalcohols are preferably stripped off at 700 to 10 mbar, preferably 400 to 70 mbar, and 60 to 90° C.

The monoalcohols can also be distilled off at atmospheric pressure in suitable evaporation devices (e.g. thin-film evaporator) at temperatures up to 120° C.

Surprisingly, it has been found that the compositions according to the invention can also be prepared "in situ" by alkylation of i) at least one tertiary amine $NR_1R_2R_3$, where $R_1$ is an unbranched or branched alkyl or alkenyl group having 12 to 36 carbon atoms, a group $R_5CONH(CH_2)_n$— or a group $R_5COO(CH_2)n$—, where $R_5$ is an alkyl or alkenyl group having 12 to 36 carbon atoms and n is a number from 1 to 8, and $R_2$ and $R_3$, independently of one another, may be identical or different and are $CH_3$—, $CH_3CH_2$—, $CH_3CH_2CH_2$—, $CH_3CH_2CH_2CH_2$— or —$CH_2CH_2(OH)$, by ii) at least one alkylating agent chosen from a) $R_4X$, where $R_4$ is —$CH_3$, $CH_3CH_2$—, $CH_3CH_2CH_2$—, $CH_3CH_2CH_2CH_2$— or —$CH_2CH(OH)CH_2(OH)$, and X is Cl, I, Br, $OSO_3H$ or methosulfate, and/or b) ethylene oxide and an acid HX, where X is Cl, I, Br, $OSO_3H$, citrate or lactate, in the presence of iii) at least one polyhydric alcohol b) having 5 to 12 carbon atoms and iv) optionally at least one unbranched or branched monoalcohol having 1 to 4 carbon atoms.

Preferably, in the reaction, the feed amounts of polyhydric alcohols b) and optionally unbranched or branched monoalcohols having 1 to 4 carbon atoms are chosen to correspond to the compositions already described above as preferred for the compositions according to the invention. The contents can also be adjusted by subsequent addition or removal of the components.

In a preferred embodiment, no unbranched or branched monoalcohols having 1 to 4 carbon atoms are used in the reaction.

The compositions according to the invention prepared by the above-described processes can be converted as homogeneous or inhomogeneous melts by cooling into pellets, flakes, extrudates or pastes or, after cooling, be further processed to give compacts, powders, granulates, emulsions or dispersions.

The compositions are preferably further processed into pellets or flakes, particularly preferably pellets.

The compositions according to the invention are generally suitable for the preparation of compositions comprising quaternary ammonium compounds.

The compositions are particularly suitable for the preparation of cosmetic, dermatological and pharmaceutical compositions.

In particular, the compositions are suitable for the preparation of hair-treatment compositions.

The invention accordingly also provides for the use of the compositions according to the invention for the preparation of compositions, preferably cosmetic, dermatological and pharmaceutical compositions, in particular hair-treatment compositions, comprising quaternary ammonium compounds.

Examples of preferred compositions are shampoos, rinse-off hair conditioners, cream rinses, clear rinses, hair cures, hair colorants and hair tints, permanent waving compositions, hair gels, hair conditioners in aerosol, spray and fluid form, 2-in-1 shower preparations, cream shower preparations, skincare compositions, day creams, night creams, care creams, nutrient creams, body lotions and ointments.

The cosmetic, dermatological and pharmaceutical compositions comprise the compositions according to the invention, based on the finished compositions, preferably in amounts of from 0.1 to 15% by weight, particularly preferably 1 to 10% by weight, particularly preferably 1 to 7% by weight.

The cosmetic, dermatological and pharmaceutical compositions can comprise, as further auxiliaries and additives, all customary surfactants, oily substances, emulsifiers and coemulsifiers, cationic polymers, film formers, super fatting agents, moisture-donating agents, stabilizers, biogenic active ingredients, preservatives, pearlizing agents, dyes and fragrances, solvents, glycerol, hydrotropic agents, opacifiers, thickeners, dispersants, protein derivatives, such as gelatins, collagen hydrolyzates, natural and synthetic-based polypeptides, egg yolk, lecithin, lanolin and lanolin derivatives, silicones, deodorizing agents, substances with a keratolytic and keratoplastic action, enzymes, carrier substances, antioxidants, UV light protection filters, pigments and metal oxides, and antimicrobially effective agents.

The surfactants used may be anionic, cationic, nonionic, amphoteric and/or zwitterionic surfactants.

Preferred nonionic surfactants contain, as hydrophilic group, a polyol group, a polyolalkenyl ether group, or a combination of polyol and polyglycol ether groups. Preference is given to addition products of from 2 to 30 mol of ethylene oxide, 2 to 30 mol of ethylene oxide together with up to 5 mol of propylene oxide or of up to 5 mol of propylene oxide onto linear fatty alcohols having 8 to 22 carbon atoms and alkylphenols having 8 to 15 carbon atoms in the alkyl group, ($C_{12}$–$C_{19}$)-fatty acid mono- and diesters of addition products of from 1 to 30 mol of ethylene oxide onto glycerol, glycerol mono- and diesters and sorbitan mono- and diesters of saturated and unsaturated ($C_8$–$C_{18}$)-fatty acids and ethylene oxide addition products thereof, ($C_8$–$C_{18}$)-alkylmono- and oligoglycosides and ethoxylated analogs thereof, addition products of from 10 to 60 mol of ethylene oxide onto castor oil and hydrogenated castor oil, ethoxylated and nonethoxylated mono-, di- and trialkyl monophosphoric esters, in particular mono-, di- and tri (lauryl tetraglycol ether) o-phosphoric esters and mono-, di- and tri(cetyl tetraglycol ether) o-phosphoric esters.

Preferred amphoteric surfactants carry a ($C_8$–$C_{18}$)-alkyl or acyl group and at least one free amino group and at least one —COOH or —$SO_3H$ group. Preference is given to N-acylglycines, N-alkylpropionic acid, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case 8 to 18 carbon atoms in the alkyl group. Particular preference is given to N-cocoalkylaminopropionate, cocoacylaminoethy-laminopropionate and ($C_{12}$–$C_{18}$)-alkylsarcosines.

Particularly suitable zwitterionic surfactants are betaines, such as, for example, N-alkyl-N,N-dimethylammonium glycinates, e.g. cocoalkyldimethylammonium glycinates, N-acylaminopropyl-N-N-dimethylammonium glycinates, e.g. cocoacylaminopropyldimethylammonium glycinate, 2-alkyl-3-carboxymethyl-3-hydroxyethylimidazolines having in each case 8 to 18 carbon atoms in the alkyl or acyl group and cocoacylaminoethyl hydroxyethylcarboxymethyl glycinate.

The compositions preferably comprise surfactant mixtures, particular preference being given to mixtures of nonionic and zwitterionic or amphoteric surfactants in a weight ratio of from 5:1 to 1:5 or mixtures of nonionogenic surfactants and any desired mixtures of zwitterionic and amphoteric surfactants in a weight ratio of from 5:1 to 1:5.

Suitable oily substances are all known oils, fats and waxes of mineral, animal, vegetable and synthetic origin. Preference is given, as oil and fatty components, to diallyl ethers having a total of 12 to 24 carbon atoms, fatty acid esters having a total of 12 to 26 carbon atoms, liquid hydrocarbons having 10 to 32 carbon atoms and mixtures thereof.

Suitable fatty acid esters are, for example, methyl palmitate, ethyl oleate, isopropyl myristate, n-hexyl laurate, n-butyl stearate and cetyl/stearyl isononanoate.

Particular preference is given to paraffin oils, vaseline, vegetable oils, synthetic triglycerides, such as, for example, glyceryl tricaprylate, and also silicone oils.

Super fatting agents which may be used are substances such as, for example, lanolin and lecithin, and polyethoxylated or acylated lanolin and lecithin derivatives, polyol fatty acid esters, monoglycerides and fatty acid alkanolamides.

Suitable bodying agents are fatty alcohols having 12 to 22, preferably 12 to 18, carbon atoms, and also partial glycerides.

Further thickeners which may be used are polysaccharides, in particular xantham gum, guar-guar, agar-agar, alginates, carboxymethylcellulose, hydroxyethylcellulose, relatively high molecular weight polyethylene glycol mono- and diesters of fatty acids, polyacrylates, polyvinyl alcohol and polyvinylpyrrolidone, surfactants such as, for example, ethoxylated fatty acid glycerides, esters of fatty acids with polyols such as, for example, pentaerythritol or trimethylpropane, fatty alcohol ethoxylates or alkyl oligoglucosides, and electrolytes, such as sodium chloride and ammonium chloride.

Examples of suitable silicone compounds are dimethylpolysiloxane, methylphenylpolysiloxanes, cyclic silicones, and amino-, fatty acid-, alcohol-, polyether-, epoxy-, fluorine- and/or alkyl-modified silicone compounds which, at room temperature, may either be in liquid form or in the form of a resin.

Biogenic active ingredients are to be understood as meaning, for example, Bisabolol®, Allantoin®, Phytantriol®, Panthenol®, AHAs, plant extracts and vitamin complexes.

Antidandruff agents which can be used are Climbazole®, Octopirox®, Oxiconazole® and Zinc Pyrethione®.

Customary film formers are chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof and similar compounds.

To improve the flow behavior, hydrotropic agents, such as, for example, ethanol, isopropyl alcohol, propylene glycol or glucose, can also be used.

Suitable preservatives are, for example, phenoxyethanol, formaldehyde solution, parabens, pentanediol and sorbic acid.

An available moisture-donating substance is, for example, isopropyl palmitate, glycerol and/or sorbitol.

The total content of auxiliaries and additives in the compositions is preferably 1 to 50% by weight, particularly preferably 5 to 40% by weight.

EXAMPLES

The examples below serve to illustrate the invention, but do not limit it.

The quat active content of the compositions according to the invention was determined by cation titration. The setting points were determined by slowly reducing the temperature.

Example 1

110.54 g of ®Genamin KDMP (behenyltrimethylammonium chloride pellets with a content of about 19% isopropanol, Clariant GmbH) were mixed into 38.37 g of dipropylene glycol in a 1000 ml round-bottomed flask and melted in an oil bath at 70–90° C. After a homogeneous melt had formed, a vacuum of initially about 700 mbar was applied on the rotary evaporator and the isopropanol was distilled off over the course of about 3 hours. For this, the vacuum was continuously increased to about 22 mbar. Subsequently, residues of the volatile solvent were removed over the course of 2 hours at a bath temperature of 90° C. and a vacuum of 16 mbar. This gave a clear solution which solidified at 69–73° C. and was present in completely molten form again at 90° C. At 25° C., the composition was wax-like solid. The quat active content was 70% by weight.

Example 2

A composition of 75% by weight of behenyltrimethylammonium chloride, 22% by weight of dipropylene glycol and 3% by weight of isopropanol was prepared analogously to example 1. This gave a clear solution which solidified at about 73–77° C. and was present in completely molten form again at 90° C. At 25° C., the composition was wax-like solid. The quat active content was 75% by weight.

Example 3

A composition of 75% by weight of behenyltrimethylammonium chloride, 23.7% by weight of 1,6-hexanediol and 1.3% by weight of isopropanol was prepared analogously to example 1. This gave a clear solution which solidified at about 71° C. and was present in completely molten form again at 90° C. At 25° C., the composition was wax-like solid. The quat active content was 75% by weight.

Example 4

®Genamin KDMP (behenyltrimethylammonium chloride pellets with a content of about 19% isopropanol, Clariant GmbH) were dried to constant weight in a vacuum furnace to remove the solvent for 14 hours at a temperature of 74° C. and a pressure of about 200 mbar (the weight loss corresponded here to the expected amount of solvent of about 19%). The pellets dried in this way were ground to a powder and sieved (sieve width: 630 $\mu$m). 4.9 g of dried and sieved behenyltrimethylammonium chloride were introduced into a 50 ml powder bottle made of glass and treated with 5.1 g of dipropylene glycol. After the bottle had been sealed, the mixture was heated at about 100° C. for 4 hours. During this period, the sample was stirred a number of times using a spatula in order to homogenize the mixture. This gave a clear solution which solidified at about 45° C. and was present in completely molten form again at 70° C. The quat active content was 49% by weight.

Example 5

A composition comprising 49% by weight of behenyltrimethylammonium chloride and 51% by weight of 1,6-hexanediol was prepared analogously to example 4. This gave a clear melt which solidified at about 42° C. and was present in completely molten form again at 70° C. At 25° C., the composition was wax-like solid. The quat active content was 49% by weight.

Formulation examples of cosmetic formulations:

The composition according to the invention from example 3 was melted and pelletized by being dropped onto a cold metal plate. The pellets obtained in this way were then incorporated into the corresponding formulations.

Example 6

Cream Rinse

| | | |
|---|---|---|
| A | Composition from Ex. 3 | 2% by weight |
| | ® HOSTAPHAT KL 340 D | 1.5% by weight |
| | (trilaureth-4 phosphate, Clariant) | |
| | Cetyl alcohol | 3% by weight |
| | Paraffin oil | 1% by weight |
| B | Water | 92.5% by weight |
| C | Citric acid | q.s. |
| | Preparation: | |
| I) | Melt A at 75° C. | |
| II) | Heat B to 75° C. | |
| III) | Stir B into A and cool | |
| IV) | Adjust pH to pH = 4 using C | |

Example 7

O/W Handcream

| | | |
|---|---|---|
| A | Composition from Ex. 3 | 2.7% by weight |
| | ® HOSTACERIN DGSB | 6% by weight |
| | (PEG-4 polyglycerol-2-stearate, Clariant) | |
| | Paraffin oil, high viscosity | 10% by weight |
| | Isopropyl palmitate | 10% by weight |
| B | Water | 70.9% by weight |
| | Preservative | q.s. |
| C | Perfume | 0.4% by weight |
| | Preparation: | |
| I) | Melt A at 80° C. | |
| II) | Heat B to 80° C. | |
| III) | Stir B into A and cool | |
| IV) | Add C at 35° C. | |

Example 8

Hair Conditioner with Pearlescent Effect

| | | |
|---|---|---|
| A | Composition from Ex. 3 | 2% by weight |
| | ® Genamin KSL | 9% by weight |
| | (PEG-5 stearyl ammonium lactate, Clariant) | |
| | ® Hostaphat KL 340 D | 1.5% by weight |
| | (trilaureth-4 phosphate, Clariant) | |
| | Jojoba oil | 1.0% by weight |
| B | ® Tylose H 100 000 YP2 | 1.5% by weight |
| | (Hydroxyethylcellulose, Clariant) | |
| C | Water | ad 100% |
| D | Perfume | 0.50% |
| | Panthenol | 0.50% |
| | ® Genapol PDC | 4% by weight |
| | (Glycol distearate, laureth-4, cocamidopropyl betaine, mica and titanium dioxide, Clariant) | |
| E | Citric acid | q.s. |
| | Preparation: | |
| I) | A is heated to 75° C. | |

-continued

II) B is carefully dissolved in C and heated to about 75° C.
III) II is added to I with stirring
IV) Leave to cool with stirring, add D to III at 30° C.
V) Adjust pH to pH = 4 using E

What is claimed is:

1. A composition comprising
a) 60 to 90 weight percent based on the composition of at least one quaternary ammonium compound according to formula (1)

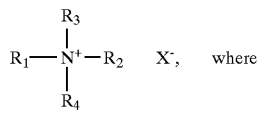

$R_1$ is an unbranched or branched alkyl or alkenyl group having 12 to 36 carbon atoms, a group $R_6CONH(CH_2)_n$— or a group $R_5COO(CH_2)_n$—, where $R_6$ is an alkyl or alkenyl group having 12 to 36 carbon atoms and n is a number from 1 to 8, and $R_2$, $R_3$ and $R_4$, independently of one another, may be identical or different and are a —$CH_3$, $CH_3CH_2$—, $CH_3CH_2CH_2$—, $CH_3CH_2CH_2CH_2$—, $CH_2CH_2OH$ or —$CH_2CH(OH)CH_2OH$ group and $X^-$ is an anion, and b) at least one polyhydric alcohol having 5 to 12 carbon atoms wherein said composition is in the form of a pellet or a flake and said composition is essentially free from fatty alcohols and unbranched or branched monoalcohols having 8 to 36 carbon atoms.

2. The composition as claimed in claim 1, wherein the quaternary ammonium compounds a) are ($C_{12}$–$C_{36}$)-alkyltrimethylammonium compounds.

3. The composition as claimed in claim 1, wherein the anion $X^-$ in formula (1) is selected from the group consisting of chloride, iodide, bromide, methosulfate, hydrogensulfate, lactate, citrate, and mixtures thereof.

4. The composition as claimed in claim 1, wherein the quaternary ammonium compound a) is behenyltrimethylammonium chloride.

5. The composition as claimed in claim 1, wherein said polyhydric alcohol b) is 10 to 40% by weight of said composition.

6. The composition as claimed in claim 1, wherein the polyhydric alcohol is selected from the group consisting of pentanediol, hexanediol, hexylene glycol, trimethylpentanediol, heptanediol, octanediol, nonanediol, decanediol, undecanediol, dodecanediol, diglycerol, triglycerol, dipropylene glycol, tripropylene glycol, sorbitol, xylitol, mannitol, and mixtures thereof.

7. The composition as claimed in claim 1, wherein the polyhydric alcohol is select from the group consisting of 1,5-pentanediol, 1,2-pentanediol, 1,6-hexanediol. 1,2-hexanediol, 1,7-heptanediol. 1,2-heptanediol, 1,8-octanediol, 1,2-octanediol, 1,9-nonanediol, 1,2-nonanediol, 1,10-decanediol, 1,2-decanediol, 1,11-undecanediol, 1,2-undecanediol, 1,12-dodecanediol, 1,2-dodecanediol, 2-methyl-2,4-pentanediol, 2,2,4-trimethyl-1,3-pentanediol, diglycerol, triglycerol, dipropylene glycol, tripropylene glycol, sorbitol, xylitol, mannitol, and mixtures thereof.

8. The composition as claimed in claim 1, wherein the polyhydric alcohol is selected from the group consisting of 1,6-hexanediol, 2-methyl-2,4-pentanediol, 2,2,4-trimethyl-1,3-pentanediol, dipropylene glycol, and mixtures thereof.

9. The composition as claimed in claim 1, wherein the at least one polyhydric alcohol b) has 6 to 8 carbon atoms.

10. The composition as claimed in claim 1, which further comprises, based on a finished composition, less than 5% by weight, of unbranched or branched monoalcohols having 1 to 4 carbon atoms.

11. The composition as claimed in claim 10, wherein the monoalcohols are selected from the group consisting of ethanol, propanol, isopropanol, butanol, isobutanol, tert-butanol, and mixtures thereof.

12. The composition as claimed in claim 1, which has a setting point below 100° C.

13. The composition as claimed in claim 1, which has a flash point above 80° C.

14. A process for the preparation of the composition of claim 1, which comprises preparing a mixture comprising mixing
i) 60 to 90 weight percent based on the composition of at least one quaternary ammonium compound a), and
ii) at least one polyhydric alcohol having 5 to 12 carbon atoms, and pelletizing or flaking said mixture to provide said pellet or flake.

15. A process for the preparation of a composition as claimed in claim 1, which comprises alkylating
i) at least one tertiary amine $NR_1R_2R_3$, where $R_1$ is an unbranched or branched alkyl or alkenyl group having 12 to 36 carbon atoms, a group $R_5CONH(CH_2)_n$— or a group $R_5COO(CH_2)_n$—, where $R_5$ is an alkyl or alkenyl group having 12 to 36 carbon atoms and n is a number from 1 to 8, and $R_2$ and $R_5$, independently of one another, may be identical or different and are —$CH_3$, $CH_3CH_2$—, $CH_3CH_2CH_2$—, $CH_3CH_2CH_2CH_2$— or —$CH_2CH_2(OH)$, by
ii) at least one alkylating agent chosen from
a) $R_4X$, where $R_4$ is —$CH_3$—, $CH_3CH_2$—, $CH_3CH_2CH_2$—, $CH_3CH_2CH_2CH_2$— or —$CH_2CH(OH)CH_2(OH)$, and X is Cl, I, Br, $OSO_3H$ or methosulfate, and/or
b) ethylene oxide and an acid HX, where X is Cl, I, Br, $OSO_3H$, citrate or lactate,
in the presence of
iii) at least one polyhydric alcohol having 5 to 12 carbon atoms.

16. The composition as claimed in claim 1, wherein the quaternary ammonium compound a) is 60 to 85% by weight of said composition.

17. The composition as claimed in claim 1, wherein the quaternary ammonium compounds is 60 to 82% by weight of said composition.

18. The composition as claimed in claim 1, wherein the quaternary ammonium compound a) is ($C_{14}$–$C_{24}$)-alkyltrimethylammonium compounds.

19. The composition as claimed in claim 1, wherein the quaternary ammonium compound a) is ($C_{16}$–$C_{24}$)-alkyltrimethylammonium compounds.

20. The composition as claimed in claim 1, wherein the anion $X^-$ in formula (1) is selected from the group consisting of chloride, methosulfate, and mixtures thereof.

21. The composition as claimed in claim 1, wherein the polyhydric alcohol is at least 15% by weight of said composition.

22. The composition as claimed in claim 1 wherein less than 3% by weight of said composition is unbranched or branched monoalcohols having 1 to 4 carbon atoms.

23. The composition as claimed in claim 10, wherein the monoalcohols comprise isopropanol.

24. The composition as claimed in claim 1, which has a setting point below 95° C.

25. The composition as claimed in claim 1, which has a setting point below 90° C.

26. The composition as claimed in claim 1, which has a setting point below 85° C.

27. The composition as claimed in claim 1, which has a flash point above 100° C.

28. The composition as claimed in claim 1, which is in a form of pellets.

29. The process of claim 14, wherein component i) contains a branched or unbranched monoalcohol having 1 to 4 carbon atoms, said monoalcohol being removed from component i) prior to said mixing step.

30. The process of claim 14, further comprising adding to the mixture at least one unbranched or branched monoalcohol having 1 to 4 carbon atoms and removing said monoalcohol from the composition alter said mixing step.

31. The process of claim 15, further comprising alkylating said tertiary amine in the presence of at least one unbranched or branched monoalcohol having 1 to 4 carbon atoms, and removing said monoalcohol after said alkalating step.

32. A cosmetic preparation comprising the composition of claim 1.

33. A dermatological preparation comprising the composition of claim 1.

34. A pharmaceutical preparation comprising the composition of claim 1.

35. A hair-treatment preparation comprising the composition of claim 1.

36. A hair-treatment composition as defined in claim 35 in the form of shampoos, rinse-off hair conditioners, cream rinses, clear rinses, hair cures, hair colorants end hair tints, permanent waving compositions, hair gels and hair conditioners in aerosol form, spray form, fluid form, and mixtures thereof.

37. A process for treating hair comprising contacting hair with the hair-treatment preparation of claim 35.

* * * * *